United States Patent [19]

Ueyama et al.

[11] Patent Number: 5,342,310
[45] Date of Patent: Aug. 30, 1994

[54] SYRINGE WITH NEEDLE-HANGARING MECHANISM

[75] Inventors: Ukio Ueyama, Kobe; Shinichi Koni, Takarazuka, both of Japan

[73] Assignee: Nihon Chemical Research Co., Ltd., Kobe, Japan

[21] Appl. No.: 111,008

[22] Filed: Aug. 24, 1993

[30] Foreign Application Priority Data

Oct. 31, 1992 [JP] Japan ................. 4-316431

[51] Int. Cl.$^5$ .............................................. A61M 5/00
[52] U.S. Cl. ..................................... 604/110; 604/195
[58] Field of Search ............ 604/110, 187, 192, 198, 604/218, 263, 195

[56] References Cited

U.S. PATENT DOCUMENTS

| | | | |
|---|---|---|---|
| 4,795,432 | 1/1989 | Karczmer | 604/110 |
| 5,059,180 | 10/1991 | McLees | 604/110 |
| 5,147,303 | 9/1992 | Martin | 604/263 X |
| 5,195,983 | 3/1993 | Boese | 604/192 |

FOREIGN PATENT DOCUMENTS

WO90/06148  6/1990  PCT Int'l Appl. .

*Primary Examiner*—John D. Yasko
*Attorney, Agent, or Firm*—Oblon, Spivak, McClelland, Maier & Neustadt

[57] ABSTRACT

A syringe comprises, besides a barrel, a plunger and a needle, a needle holding stopper, a needle hole stopper, a spring connecting the needle holding stopper and needle hole stopper and a lock mechanism provided between the barrel and the needle holding stopper. The lock mechanism functions such that it fixes the needle holding stopper until completion of injection so that the needle is not pushed up into the hinder part of the barrel, and that it is released when the plunger is further pressed, i.e. by a single finger motion, after completion of the injection, so that the needle holding stopper is pushed up by force of the spring, thereby hangaring the needle in the barrel and, at the same time, the needle hole stopper is moved to close the needle hold on the end of the barrel. The syringe causes no accidental pricking of a finger with the needle after injection operation or oozing out of the blood or the like of the patient adhered on the needle tip.

5 Claims, 10 Drawing Sheets

SYRINGE WITH NEEDLE-HANGARING MECHANISM

BACKGROUND OF THE INVENTION

1. Field of the invention

The present invention relates to a syringe provided with a mechanism capable of hangaring the needle into itself after completion of injection.

2. Description of the prior art

Syringes are being used in a markedly large number principally in the medical field. In recent years, most syringes are of disposable type made of plastics. They have, before use, a plastic cap hung on the tip of the needle so that needle tip cannot directly touch the finger. After use, the syringes are discarded, either after remounting the cap or removal of the needle tip. In this case, after a syringe has been used after removal of the cap and before it is disposed after remounting of the cap, the needle tip that is still exposed often pricks the finger by mistake. Then, if the patient having received the injection is a carrier of a disease such as hepatitis, the disease infects. Prevention of this type infection has been a great concern among clinicians.

In Western countries, cases of AIDS infected due to the use of syringes have been reported, which breeds serious social unrest. Also in Japan, similar situation may happen in the near future.

Let us consider how such infection occurs. Before a syringe is used, pricking of the finger with the needle can never cause infection of hepatitis or the like, causing a wound though. The problem is during the period between the use of a syringe and its disposal and that between the disposal in a container and completion of final treatment of the syringe, while the syringe is handled by many persons engaged. Infection to clinical personnel can be prevented if the needle is hangared inside the syringe after use so that it will not prick the finger. Further it is important to close the fitting hole for the needle provided on the end of the syringe so that the blood or the like of the patient adhered to the needle tip will not ooze outwardly.

Considerable complexity may be required for a mechanism capable of taking out the needle from inside the syringe upon use without pricking the finger and, at the same time, hangaring the needle into the syringe after use. Few attempts have therefore been made to add this type of mechanism to conventional disposable syringes.

As an example of such attempts, WO/90/06148 discloses a mechanism which combines about 10 pieces of complex-shaped plastic molded articles inside a plastic syringe and utilizes the force of a spring, thereby taking the needle in and out. In this mechanism, when the plunger is pushed upon use, the needle housed inside the syringe springs out through the tip of the syringe and is automatically mounted thereon. Then, after sucking a medicine and injecting it into a patient, the plunger is further pushed, which releases the lock and hangars the needle into the syringe by force of the spring. Further the mechanism does not allow the needle once hangared to come out even if the plunger is pushed again.

In this mechanism, the needle has been bent beforehand, is then deformed to straighten upon use and, after use, assumes its original shape when it is withdrawn. The needle thus bent again cannot comes out again even when the plunger is pressed. However, the degree of deformation cannot be sufficiently large restricted by the entire shape and hence the needle tip tends to come out to cause a danger, when parts fixing the needle shift only slightly. Another disadvantage is difficulty in completely sealing the mechanism part, thereby often allowing the medicine to penetrate thereinto. Furthermore, the mechanism contains a large number of parts and has a complex shape so that its fabrication requires a very careful, skilled adjustment.

In this mechanism, the needle is housed inside the syringe before use. However, since infection of virus or the like can never occur before use, it is not considered necessary to add such a complex mechanism for this purpose.

SUMMARY OF THE INVENTION

Accordingly, an object of the present invention is to provide a syringe provided with a mechanism capable of hangaring the needle inside it immediately after completion of injection so that the needle will not prick the fingers of clinical personnel by mistake during the period between its use and disposal and, at the same time, preventing the blood or the like of the patient adhered to the needle tip from oozing outwardly.

The present invention provides a syringe with needle-hangaring mechanism comprising a barrel 1, a plunger 2, a needle 3, a needle holding stopper 4, a needle hole stopper 5, a spring 6 connecting the needle holding stopper and the needle hole stopper and a lock mechanism provided between the barrel and the needle holding stopper, the barrel 1 comprising a forward part having a smaller inside diameter and a rear part having a larger diameter, the two parts being connected with each other at a connecting point 18 having an diameter difference, the lock mechanism functioning, in combination with the spring and the needle hole stopper, such that it holds the needle holding stopper, until completion of injection, so that the needle holding stopper is not pushed up into the hinder part of the barrel, and that it is released when the plunger is further pressed after completion of the injection, so that, by force of the spring, the needle holding stopper is pushed up, thereby hangaring the needle in the barrel, and, at the same time, the needle hole stopper is moved to stopper the needle hole on the barrel end.

According to the present invention, it becomes possible to, after use of the syringe, hangar the needle into the barrel to ensure safety by a single finger motion.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 2 (*a*) is an enlarged vertical cross-sectional view of the needle holding stopper and lock mechanism of the syringe before use shown in FIG. 1 and (*b*) is an enlarged horizontal cross-sectional view of (*a*) taken on line A—A';

FIG. 3 (*a*) is an enlarged vertical cross-sectional view of the needle holding stopper and lock mechanism of the syringe after use shown in FIG. 1 and (b) is an enlarged horizontal cross-sectional view of (a) taken on line A—A';

FIG. 5 (a) is an enlarged vertical cross-sectional view of the needle holding stopper and lock mechanism of another embodiment of the syringe of the present invention, and (b) shows an enlarged horizontal cross-sectional view of (a) taken on line A—A';

FIG. 6 (a) is an enlarged vertical cross-sectional view of the needle holding stopper and lock mechanism of the syringe after use shown in FIG. 5 and (b) is an enlarged horizontal cross-sectional view of (a) taken on line A—A';

FIG. 9 (a) and (b) are enlarged cross-sectional views taken on lines A—A' and B—B' of FIG. 8, respectively; and FIG. 10 (a) is a perspective view of the engaging part of cams provided in the syringe shown in FIG. 7, and (b), (c) and (d) show the successive positioning of the cams.

DESCRIPTION OF THE PREFERRED EMBODIMENTS

The present inventors have paid attention to the fact that, in handling a syringe, infection of virus or the like due to pricking of a finger with the syringe needle can only occur during the period immediately after completion of injection until completion of the disposal of the used syringe. The inventors have come to an idea of a simple mechanism utilizing a spring and capable of safely hangaring the needle into the syringe after completion of injection and, at the same time, closing the hole for mounting the needle provided on the end of the syringe, and completed the invention.

The present invention provides a syringe with needle-hangaring mechanism comprising a barrel 1, a plunger 2, a needle 3, a needle holding stopper 4, a needle hole stopper 5, a spring 6 connecting the needle holding stopper and the needle hole stopper and a lock mechanism provided between the barrel and the needle holding stopper, the barrel 1 comprising a forward part having a smaller inside diameter and a rear part having a larger diameter, the two parts being connected with each other at a connecting point 18 having an diameter difference, the lock mechanism functioning, in combination with the spring and the needle hole stopper, such that it holds the needle holding stopper, until completion of injection, so that the needle holding stopper is not pushed up into the rear part of the barrel, and that it is released when the plunger is further pressed after completion of the injection, so that, by force of the spring, the needle holding stopper is pushed up, thereby hangaring the needle in the barrel, and, at the same time, the needle hole stopper is moved to stopper the needle hole on the barrel end.

The present invention further provides concrete mechanisms for locking the needle holding stopper and for closing the needle hole.

Figure 1A:
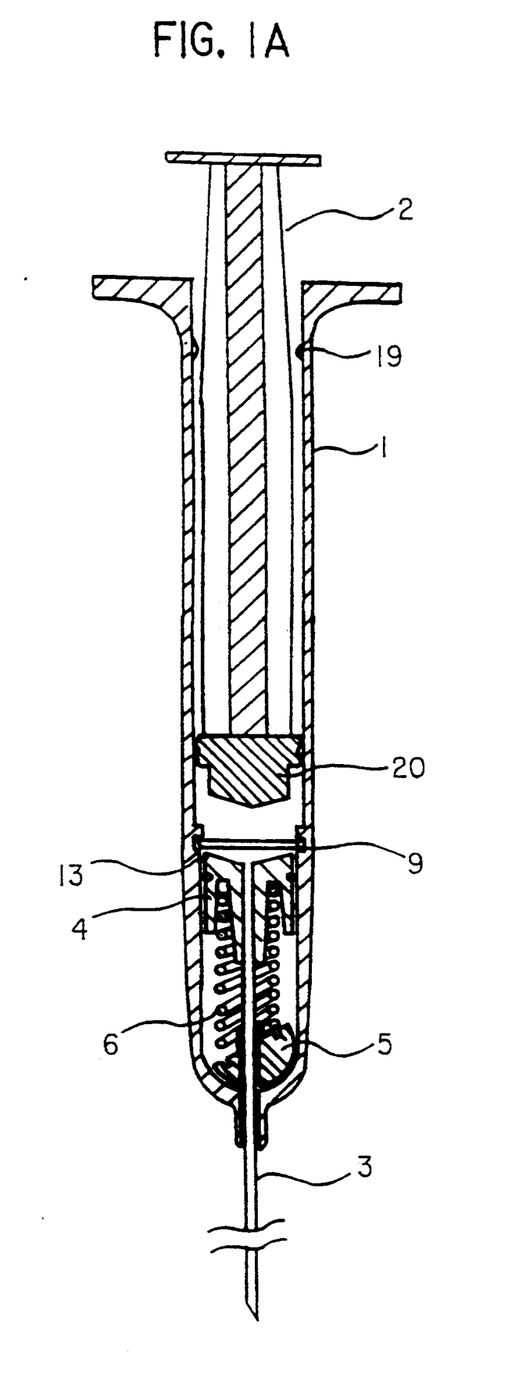
FIG. 1 is a cross-sectional view of an embodiment of the syringe with needle-hangaring mechanism of the present invention, where (*a*) and (*b*) show those before use and after use, respectively.
Figure 1B:
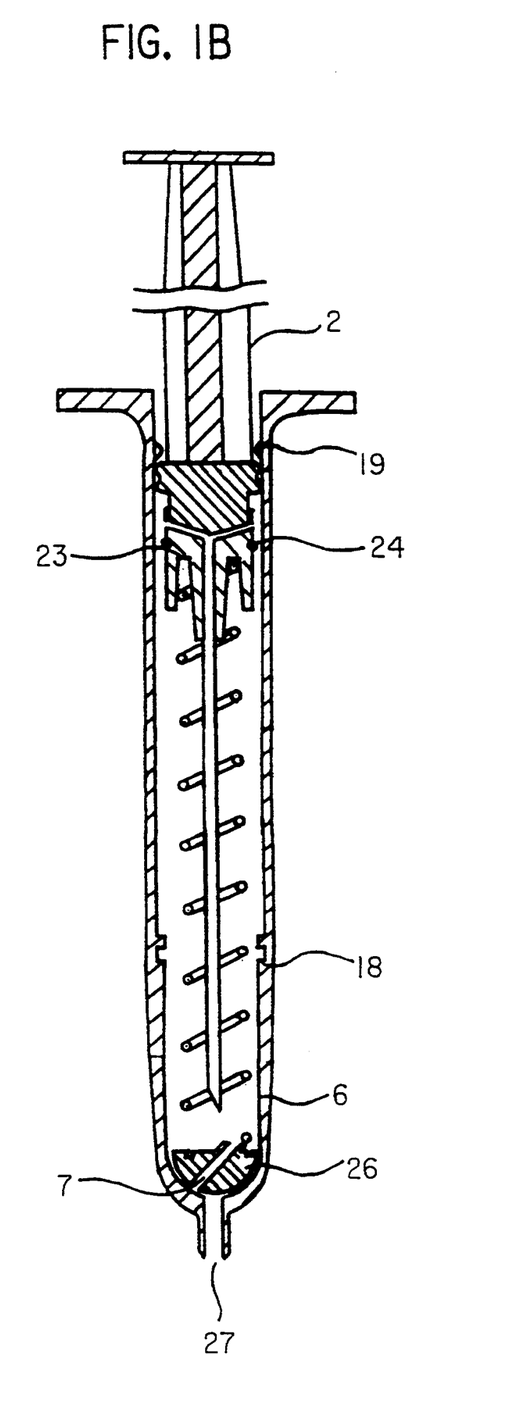

In the present invention, the phrase "push up" or "push down" the needle holding stopper means, in the syringe shown in, for example, FIG. 1, the motion to move upwardly or downwardly, respectively; that is, to push up means to move from the forward part of a syringe to the hinder part and to push down means to move from the rear part of the syringe to the forward part.

Safety measures in handling a syringe include those against infection of virus of hepatitis or the like and against simple pricking on fingers. It would then be perfect if the needle is housed in the syringe before use, mounted by a single finger motion upon use and, after use, hangared inside the syringe again by a single finger motion so that the blood or the like adhered on the needle tip does not ooze outwardly. This, however, inevitably requires a considerably complex mechanism, which is all the more uneconomical because most syringes in recent years are of a disposable type.

When the degree of injury caused by the needle of a syringe is considered, a simple finger prick is very insignificant compared with infection of virus or the like and may be acceptable. Infection of virus or the like should be completely prevented by a mechanism which comprises hangaring the needle safely by a single finger motion, keeping the needle tip from coming outwardly again even when a strong force is applied, and preventing the blood or the like adhered to the needle chip from oozing outwardly; while allowing the possibility of a slight finger prick. Such a mechanism, concentrating on prevention of infection, should be much simplified.

Based on the above concept, the syringe of the present invention has been completed to simplify its mechanism significantly and is provided, in the inside of the barrel, with a movable needle holding stopper and its lock mechanism that is releasable, and with a spring which connects the needle holding stopper and the needle hole stopper, and utilizes the force of the spring to hangar the needle and close the needle hole.

Other features of the invention will become more apparent in the course of the following descriptions of exemplary embodiments which are given for illustration of the invention and are not intended to be limiting thereof.

Several embodiments of the present invention are concretely described by reference to the drawings.

FIG. 1 (a) and (b) are cross-sectional views of an embodiment of the syringe of the present invention before use and after use, respectively. The barrel 1 and plunger 2 of the syringe are, like for conventional syringes generally used, of any material insofar as it is transparent and contains no ingredients that can dissolve out into the medicine used. In general, a plastic or glass is used for this purpose. While glass is chemically more stable than plastics, it is expensive and difficult to process into complex shapes. On the other hand, plastics are readily processable into complex shapes and inexpensive. For this reason, most disposable syringes are made of plastics in recent years. The end of the plunger is covered with a synthetic or natural rubber, a highly elastic plastic or the like to ensure high airtightness.

It is desirable that the syringe of the present invention be made of a readily processable plastic, since the syringe should be provided in the inside thereof with a mechanism for housing the needle, and that the plunger end be covered with rubber or the like to ensure high airtightness. The barrel 1 comprises a forward part having a smaller inside diameter and a rear part having a larger inside diameter connected with each other via a point 18 with diameter difference. The inner surface of the hinder part of the barrel is provided with a pair of recesses 8 and 8' which is an element of a lock mechanism for keeping the needle holding stopper 4, until completion of injection, from being pushed up toward the hinder part of the barrel. A stopper 19 for preventing the plunger from falling out is provided near the backward end of the barrel.

On the end of the plunger 2 is mounted a rubber packing 20, which comprises, from the forwardest side, a conical part 10, and cylindrical parts 11 and 12 having outside diameters matching the inside diameters of the forward part and rear part of the barrel, respectively.

The needle 3 may be similar to needles of conventional syringe, except that its length is 10 to 15 mm larger than that of conventional needles because the syringe is provided therein with a mechanism for hangaring the needle.

Figure 2A:
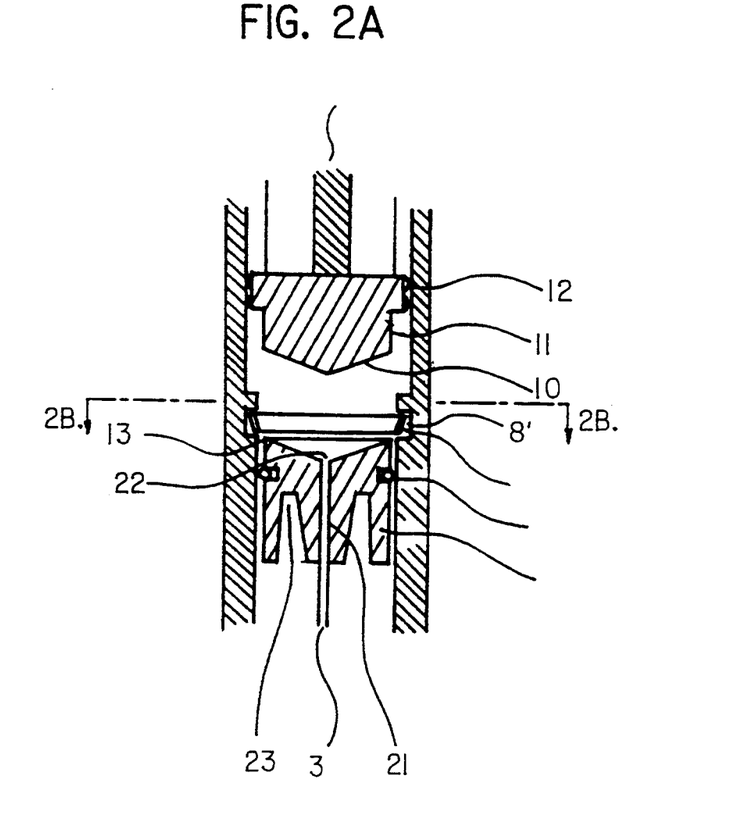

The needle holding stopper 4 holds the needle 3 and is provided with a spring support 23 for supporting one end of a spring 6, and also functions such that it is not pushed up into the rear part of the barrel by force of the spring. The stopper 4 is hence of complex shape and is therefore preferably a plastic molded article, the material being not specifically limited though. FIG. 2 (a) is an enlarged cross-sectional view of an embodiment of the needle holding stopper 4, wherein the needle is fixed by adhesion on part 21 and the injection used enters the entrance 22 of the needle 3 and passes through the inside of the needle 3. The needle holding stopper contacts the inner surface of the forward part of the barrel via a packing 24.

The packing 24 is provided in order to increase the airtightness and can completely prevent the injection used from leaking into a space between the needle holding stopper and the forward end of the barrel.

The lock mechanism comprises a pair of recesses 8 and 8' provided on the inner surface of the syringe barrel; an elliptical lock ring 9 fit in the recesses; the packing 20 on the end of the plunger and comprising, from the forwardmost side, a conical part 10, and cylindrical parts 11 and 12 having outside diameters matching the inside diameters of the forward part and rear part of the barrel, respectively; and the backward end 13 of the needle holding stopper.

Figure 2B:
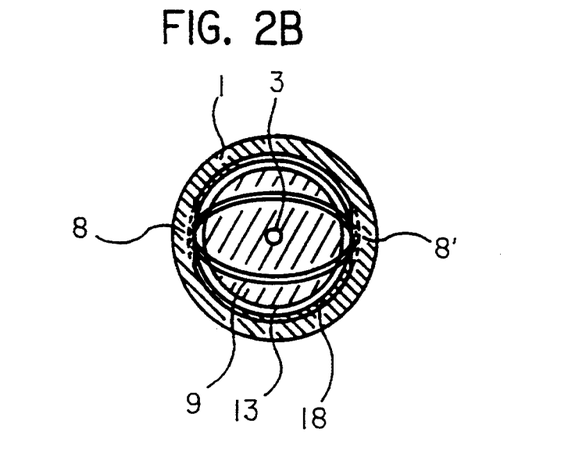
Figure 3A:
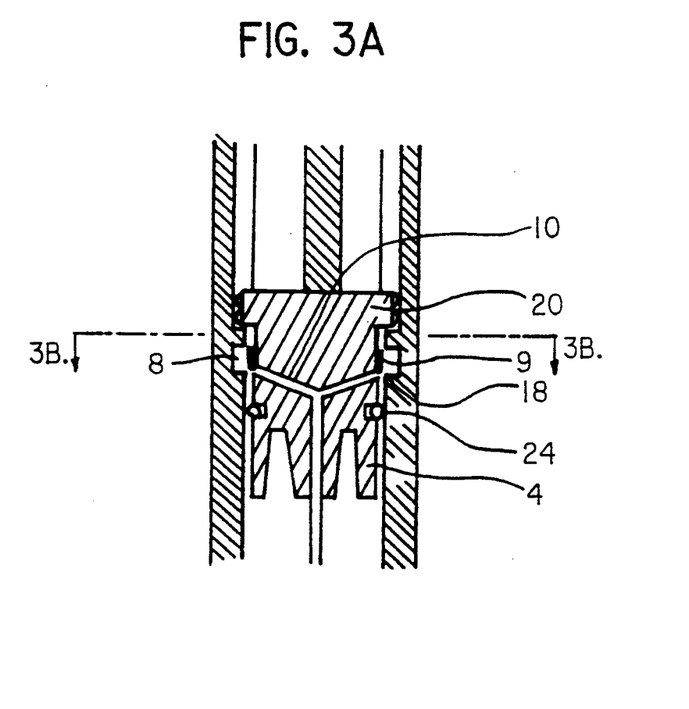
Figure 3B:
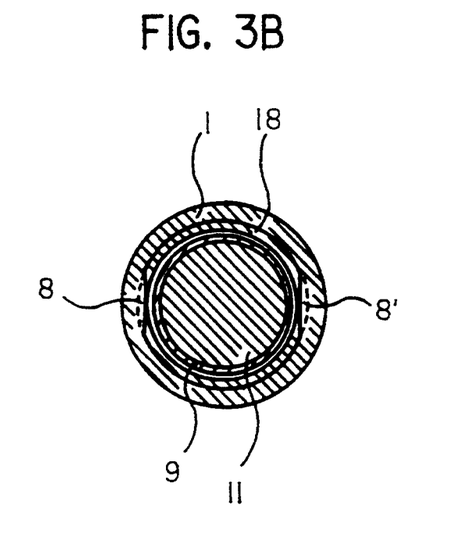

FIG. 2 (a) and (b) are an enlarged vertical cross-sectional view and its horizontal cross-sectional view taken on line A—A', respectively, of the lock mechanism before use, i.e. being locked. FIG. 3 (a) and (b) are an enlarged vertical cross-sectional view and its horizontal cross-sectional view taken on line A—A', respectively, of the lock mechanism after use, i.e. being released. Before the syringe is used, the elliptical lock ring 9 is fit in the recesses 8 and 8' provided on the inner surface of the barrel, as shown in FIG. 2 (a).

The lock ring may be of any material insofar as it is elastic and readily deformable and does not cause, when contacted with the injection used, the injection to change in quality. For example, stainless steel and elastic plastics are usable for this purpose, the former being more preferable. The lock ring preferably has a shape of ellipse as shown in FIG. 2 (b). The material for the lock ring may have any original shape but preferably is a thin stainless steel strip or a stainless steel wire. Among a variety of possible lock rings, particularly preferable shape is an elliptic hollow cylinder with its wall being thin and readily deformable and its side contacting the upper part of the recesses 8 and 8' outwardly tapering a little, as shown in FIG. 2 (a). This type of shape ensures high locking capability.

The needle holding stopper 4 is pushed up from underneath by a spring 6 and its upper end 13 is, as shown in the horizontal cross-sectional view of FIG. 2 (b), stopped by the ellipse of the lock ring. To introduce a medicine into the syringe, sometimes, at first air is pressed by the syringe into a bottle containing the medicine to increase the internal pressure, which is then utilized to charge the syringe with the medicine. In this case, the internal pressure of the syringe increases when air is being introduced into the bottle. The thus increased pressure pushes the needle holding stopper down to a point where the force of spring 6 and the internal pressure balance with each other, while the lock ring is maintained at the original position so that the lock is not released. After this operation, the internal pressure decreases, which causes the needle holding stopper to be pushed up again to reach the original position.

The plunger is then lifted up to suck the medicine into the syringe and injection is now ready. When the injection is almost complete, the end of the plunger, the lock ring and the needle holding stopper are in positions as shown in FIG. 2 (a) and (b), like those before use. Then, further pressing of the plunger causes, as shown in FIG. 3 (a) and (b), the conical end 10 of the plunger contacts the minor-axis-side wall of the elliptic lock ring. When the pressing further proceeds, the elliptic lock ring is expanded to become nearly circular and is finally fit on the cylindrical part 11 of the plunger packing, whereby the lock is released. Even when the pressing still further proceeds, the lock ring fit on the packing part 11 is stopped at the point 18 with diameter difference so that the lock ring shifts its position only a little and is maintained at nearly the original position.

Next, the pressing of the plunger is released. Then, while spring 6 pushes up the needle holding stopper, the lock ring, which is fit on the part 11 of the plunger end and hence has a decreased diameter, does not lock again when passing the recesses 8 and 8' and is pushed up to a point where the spring resumes the original form. Through the above procedure, the needle 3 is hangared in the barrel. FIG. 1 (b) shows how the needle is hangared in the barrel.

Figure 4A:
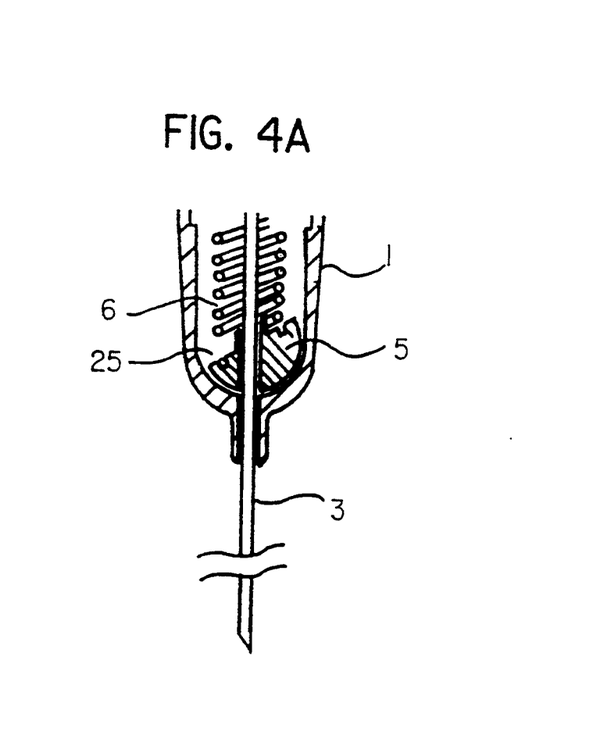
FIG. 4 is an enlarged cross-sectional view of the end part of the embodiment of the syringe of the present invention, where (a) and (b) show those before use and after use, respectively.
Figure 4B:
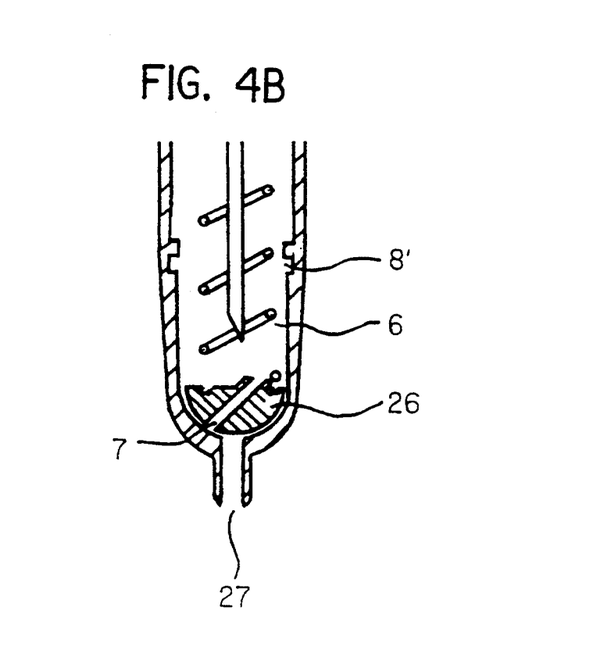

FIG. 4 (a) and (b) show the conditions of the barrel end and needle hole stopper before use and after use, respectively. The needle hole stopper 5 is provided with a small hole 7 and a spring support 25, which is connected to the spring 6. The needle hole stopper thus has a complex shape and is hence preferably a plastic molded product, the material being not specifically limited though. The needle 3 is, in the original state, penetrating the small hole 7 of the needle hole stopper 5 and maintained thereon. Then the needle is pushed up and gets out of the small hole. Instantaneously, the spring acts to push down the needle hole stopper so that the hole stopper rotates while being pushed down from the position 5 to position 26, which closes the needle hole 27 provided on the end of the barrel. The hole stopper is fixed in the state of position 26 by action of the spring.

The spring 6 may be of any material with no specific restrictions insofar as it is highly elastic and, when contacted with the injection used, is not damaged by corrosion or does not cause the injection to change in quality. Stainless steel and plastics are usable for this purpose, with the former being preferable.

The needle hole stopper may be of any shape that ensures closing of the needle hole when the needle is withdrawn from the small hole.

Figure 5A:
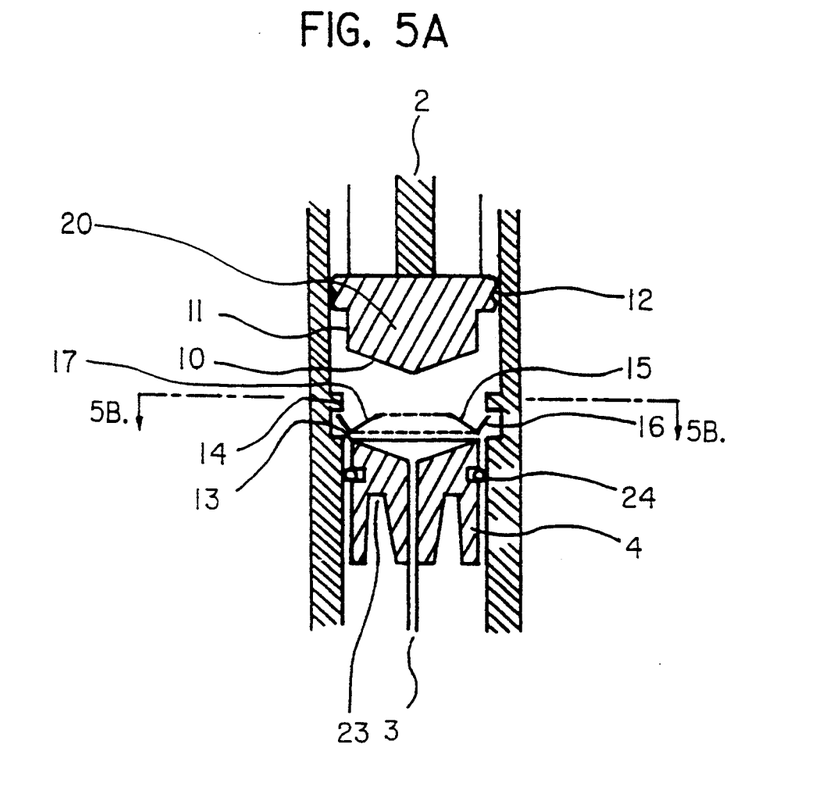
Figure 5B:
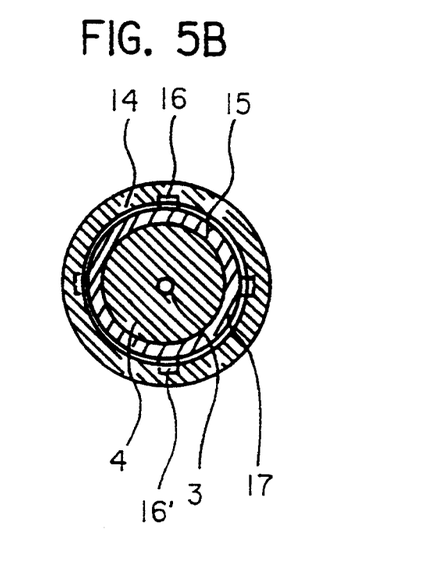

A second embodiment of the lock mechanism used in the present invention is described next. FIG. 5 (a) and (b) is an enlarged cross-sectional view and its horizontal cross-sectional view taken on line A—A' of the lock mechanism before use, i.e. being locked, respectively, while FIG. 6 (a) and (b) those after use, i.e. being released.

The lock mechanism comprises a ring-shaped projection 14 provided on the inner surface of the rear part of the barrel, a stopper 17 comprising a hollow cylinder 15 with its thin wall inclined inwardly upwardly and at least 2 small strips 16 and 16' with their tips inclined outwardly and mounted on the large diameter-side circumference of the hollow cylinder, a conical end 10 of the plunger covered with rubber packing and the backward end 13 of the needle holding stopper.

Before use of the syringe, the stopper 17 is engaged with the ring-shaped projection 14 provided on the inner surface of, and having been integrally molded with, the barrel. The stopper comprises the hollow cylinder 15 with its thin wall tapering to smaller diameter upwardly and 2 small strips 16 and 16' with their tips inclined outwardly and mounted on the large diameter-side circumference of the hollow cylinder and is engaged, with the part of the strips 16 and 16' with the projection 14. While the needle holding stopper is pressed upwardly by spring 6, the backward end 13 of the holder is held by the cylindrical part 15 of the stopper so that it cannot be pushed up into the hinder part of the barrel.

The stopper 17 may be of any material insofar as it is highly elastic and readily deformable and, when contacted with the injection used, does not cause the injection to change in quality. For example, stainless steel and elastic plastics are usable for this purpose, the former being more preferable. The stopper 17 preferably has such a structure that it comprises a thin-walled hollow cylinder 15 tapering inwardly toward the rear part of the barrel and 2 strips 16 and 16' with their tips inclined outwardly and mounted on the large diameter-side circumference of the hollow cylinder. The tapered cylinder may be a slice from a hollow cone or hollow sphere, the latter being functionally more preferable. It is necessary that at least 2 pieces of the strips be mounted on the large diameter-side circumference of the hollow cylinder, and a multiplicity of such strips may be mounted.

The needle holding stopper 4 is pressed upwardly from underneath by spring 6 and its upper end 13 is, as shown in the horizontal cross-sectional view of FIG. 5 (b), stopped by the cylindrical part 15 of the stopper 17. The strips 16 and 16' mounted on the cylindrical part 15 are engaged with the ring-shaped projection 14. It is often the case that, in order to introduce a medicine into the syringe, prior to sucking the medicine into the syringe, air is pressed by the syringe into a bottle containing the medicine to increase the internal pressure, which is then utilized to charge the syringe with the medicine. When air is introduced into the bottle, the internal pressure of the syringe increases. The thus increased pressure pushes the needle holding stopper down to a point where the force of spring 6 and the internal pressure balance with each other, while the stopper 17 is maintained in the original shape so that the lock is not released. After this operation and when the internal pressure decreases, the needle holding stopper is again pushed up to return to the original position.

Figure 6A:
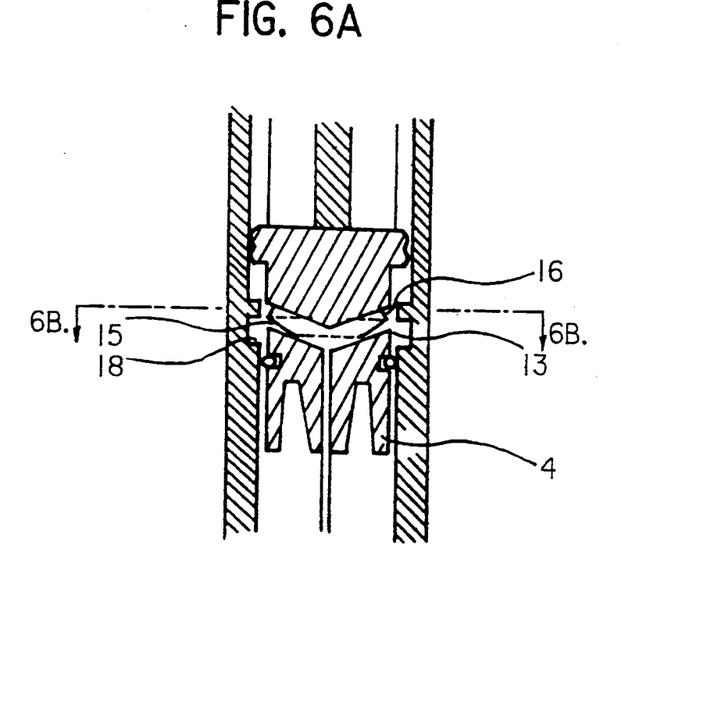
Figure 6B:
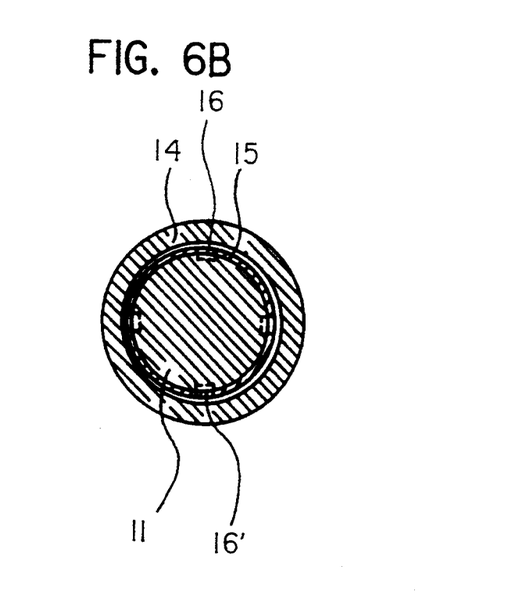

The plunger 2 has on its end a synthetic rubber packing 20 which comprises, from the forwardest side, a conical part 10 and cylindrical parts 11 and 12 having outside diameters matching the inside diameters of the forward part and rear part of the barrel, respectively. After completion of injection, when the plunger is further pushed down, the down-moving cone 10 of the packing causes the cylindrical part of the stopper 17 to be turned back, thereby bending the strips 16 inwardly to cause the lock to be released. The states of the projection on the inner surface of the barrel, the stopper 17, the needle holding stopper and the end of the plunger are shown in FIG. 6 (a) and (b). When the plunger is further pushed down, the stopper 17 on the cone part 10 of the plunger is stopped at the position of diameter difference 18 and is hence maintained at nearly the original position, not appreciably shifting therefrom.

Next, the force pressing the plunger is reduced. Then, while the spring 6 pushes up the needle holding stopper, the stopper 17, with its cylindrical part still turned back and its strips still bent inwardly, passes the position of the projection 14 without being locked again and is pushed up until the spring resumes its original shape. Through this procedure the needle 3 is hangared in the barrel. The state of the needle thus hangared is almost the same as shown in FIG. 1 (b).

Figure 7A:
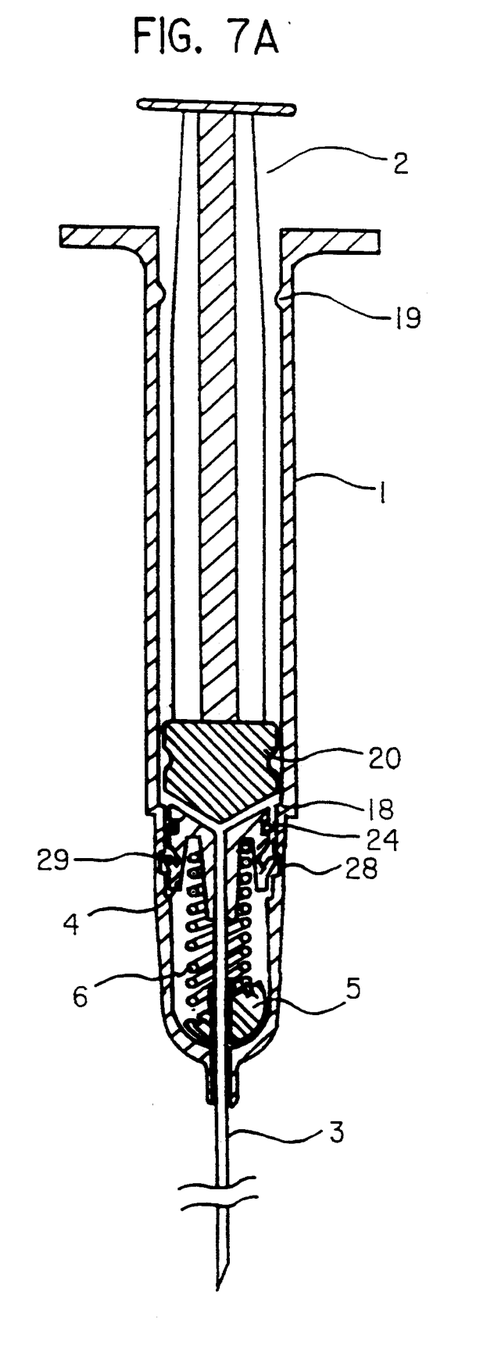
FIG. 7 is a cross-sectional view of a still another embodiment of the syringe with needle-hangaring mechanism of the present invention, where (a), (b) and (c) show those before use, with a medicine sucked into the barrel and with the needle having been hangared thereinto after use, respectively.
Figure 7B:
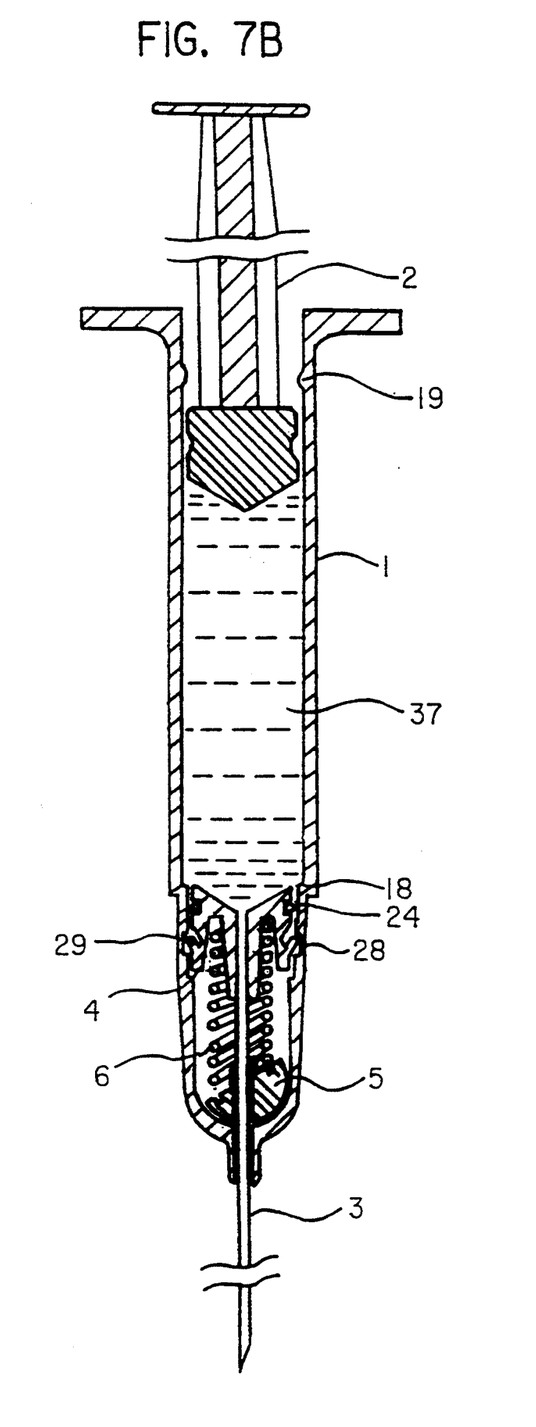

FIG. 7 (a), (b) and (c) are cross-sectional views of a third embodiment of the syringe of the present invention, where (a), (b) and (c) show that before use, that with its barrel having sucked a medicine 37 and that with the needle having been hangared in the barrel, respectively. The barrel is provided on the inner surface of its forward part a recess 28, which is part of a lock mechanism for fixing the position of the needle holding stopper 4 and, on the inner surface of its rear part, a stopper 19 for preventing the plunger from slipping off.

Figure 8:
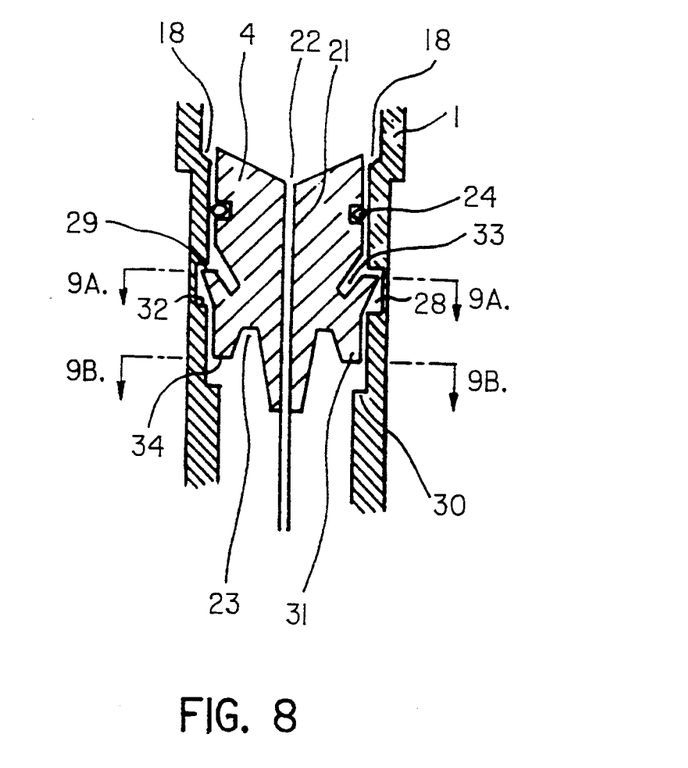
FIG. 8 is an enlarged cross-sectional view of the needle holding stopper and lock mechanism of the syringe shown in FIG. 7.

The needle holding stopper 4 has, besides the function of holding the needle, those of locking itself on the barrel and supporting one end of the spring 6. The holding stopper is hence of complex shape and is therefore preferably a plastic molded product, the material being not specifically limited though. FIG. 8 is an enlarge cross-sectional view of an embodiment of such needle holding stopper, where the needle is fixed by adhesion on part 21 and the injection used enters at 22 and injected through the inside of the needle.

Figures 9A, 9B:
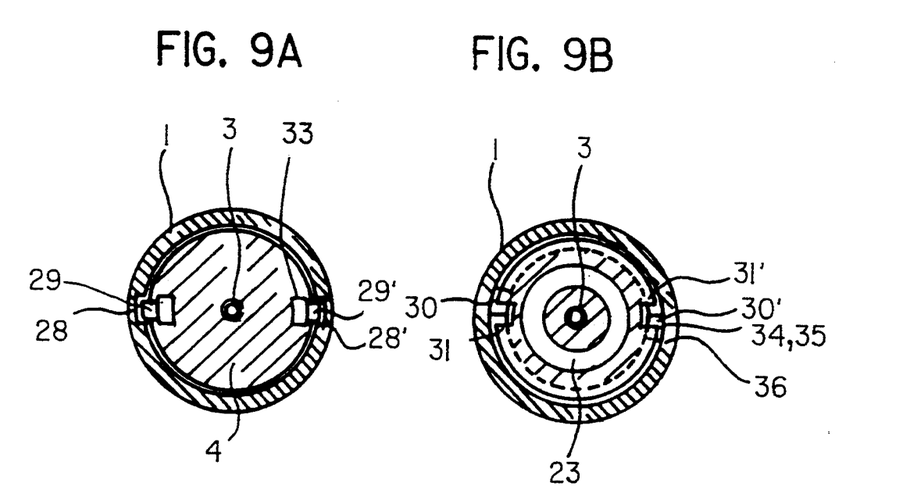
Figure 10A:
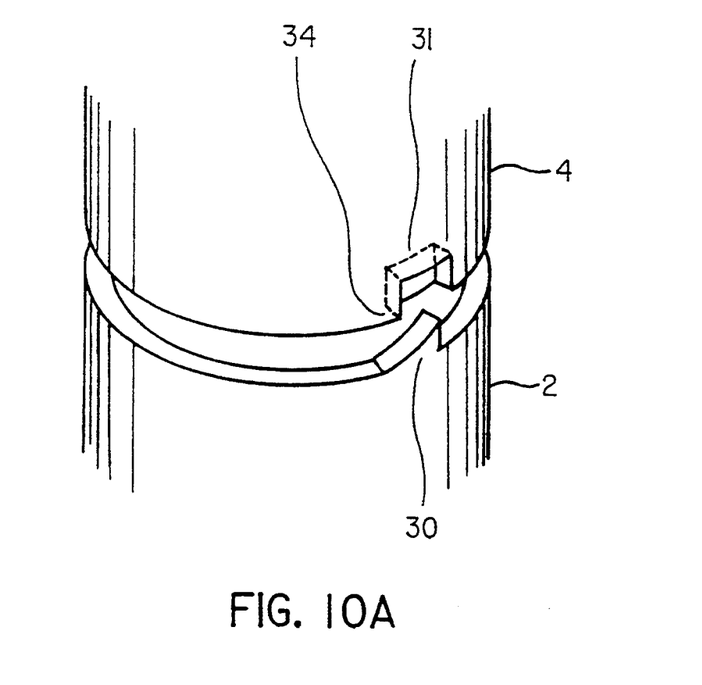
Figure 10B:
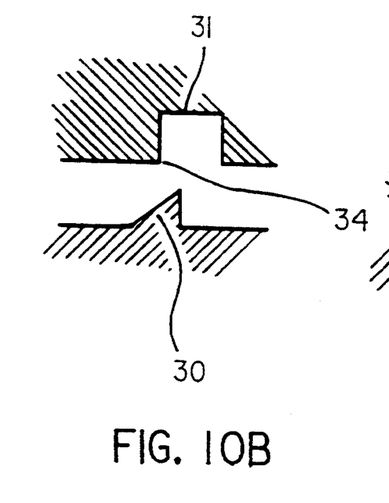
Figure 10C:
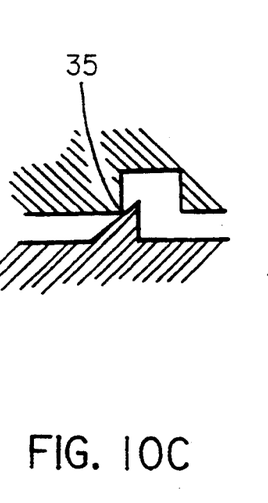
Figure 10D:
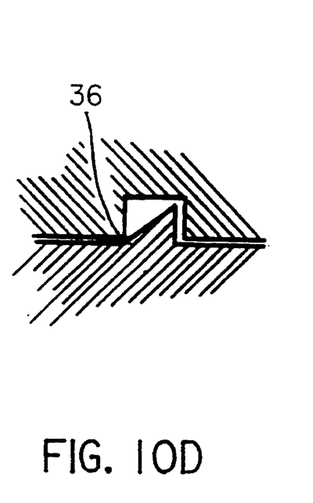

The needle holding stopper is provided on its circumference with a pair of projections 29 and 29' and the barrel is provided on its inner surface with a pair of recesses 28 and 28', as shown in FIG. 8 and FIG. 9 (a), which is a cross-sectional view taken on line A—A' of FIG. 8. The projections 29 and 29' are engaged with the recesses 28 and 28' of the barrel and, together with the force exerted by spring 6 connected to a spring support 23 (i.e. in FIG. 8 force pushing up from underneath), fix the position of the holding stopper.

When the needle holding stopper 4 is pushed down, the projections 29 contact the lower ends 32 of the recesses 28 to deform to a position of 33, thereby being disengaged from the recesses. The needle holding stopper and the barrel are provided with a pair of cams 30 and 30' and 31 and 31', respectively, on their circumferences, as shown in FIG. 9 (b), which is a cross-sectional view taken on line B—B' of FIG. 8. FIG. 10 (a) is a perspective view showing the features of the cams on one side. When the needle holding stopper is lowered, the cams 30 and 31 contact with each other and the edge 34 of the cam 31 moves down obliquely along the slope of 30 in the order of (b) to (c) and stops at the position of (d), during which the needle holding stopper rotates in an angle of circumference of 35 to 36. Then, when the pressure on the needle holding stopper is decreased and the stopper is pushed up by force of spring 6, the projections 29 no longer engage with the recesses 28, whereby the holding stopper is pushed up to a point where the spring resumes the original shape.

The needle holding stopper 4 can, as required, be provided on its circumference with a packing 24, which increases the airtightness of the contacting part between the needle holding stopper and the inner surface of the barrel, thereby completely preventing the injection from leaking in a space between the needle holding stopper and the forward end of the barrel.

The barrel is provided with a diameter difference at a point 18, in FIG. 7, where the nearly top end of the needle holding stopper 4 contacts the inner surface of the barrel. Thus, the lower part, i.e. the forward part of the syringe has a smaller inside diameter than that of the hinder part. The end 20 of the plunger 2 contacts the barrel at its large-inside-diameter part and keeps airtightness, while the needle holding stopper 4 contacts the barrel at its small-inside-diameter part, with the packing 24 ensuring airtightness.

After completion of injection and when the plunger 2 is further pressed, the lock having fixed the needle holding stopper 4 is released so that the needle holding stopper is pushed down. Then, when the force pressing the plunger is decreased, the spring 6 pushes up the needle holding stopper. On this occasion, the spring should overcome frictional resistance generating between the packing 24 of the needle holding stopper and the inner surface of the barrel and that between the end 20 of the plunger 2 and the inner surface of the barrel. Provision of the inner diameter difference 18 on the inner surface of the barrel, with the rear part having larger inner diameter compared with the forward part, markedly reduces the frictional resistance generating between the packing 24 of the needle holding stopper and the inner surface of the barrel, while that between the end 20 of the plunger and the inner surface of the barrel does not change.

Figure 7C:
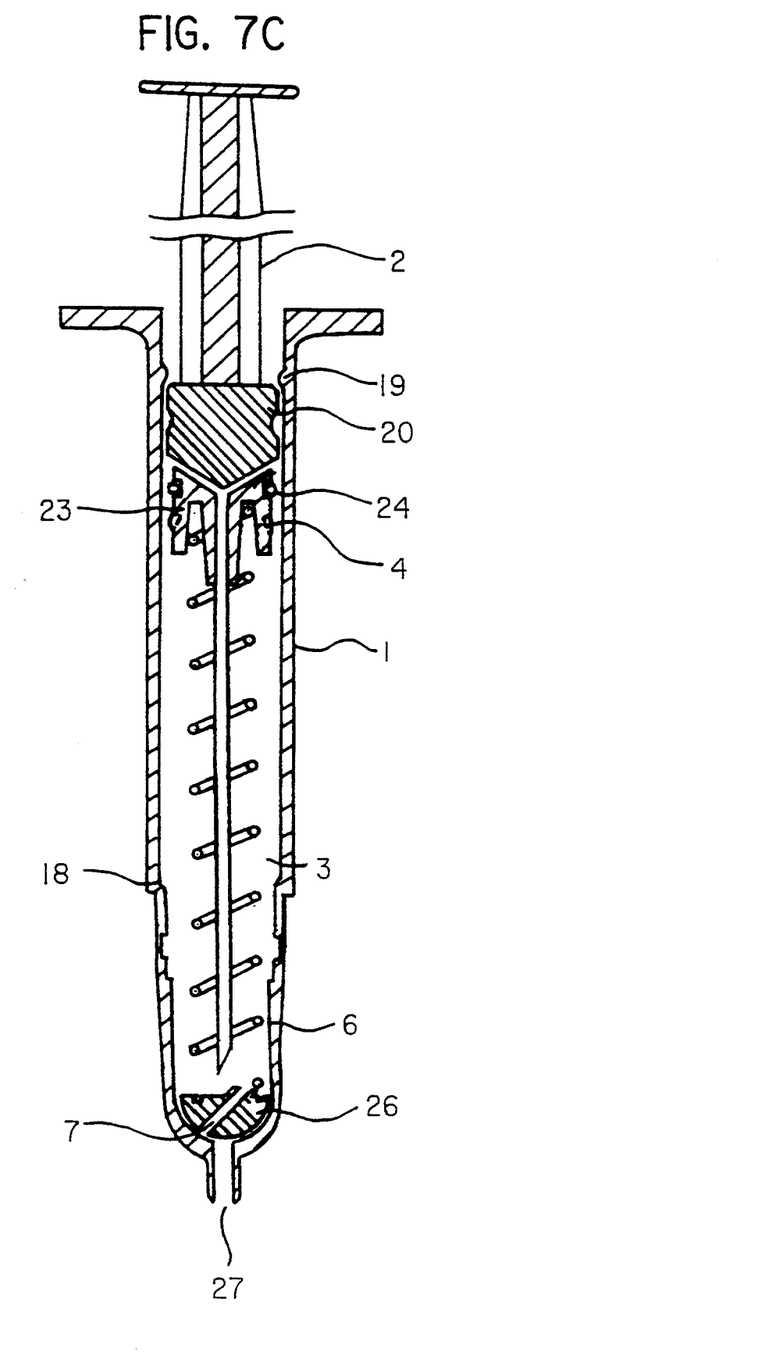

As shown in FIG. 8, the needle holding stopper contacts, at its packing 24, with the inner surface of the small-diameter-part of the barrel and maintains good airtightness. When the needle holding stopper is pushed up by spring 6, frictional resistance continue generating between the packing and the inner surface of the barrel until the packing reaches the point 18. After the packing has passed the point 18, there creates a clearance between the packing and the inner surface of the barrel due to the large inner diameter of the barrel there, whereby almost no friction occurs. As a result, the frictional resistance generating when the needle holding stopper and the plunger are pushed up decreases significantly. FIG. 7 (c) shows this state. The diameter difference of the barrel 1 is not specifically limited, but it is preferably about 1 mm for syringes for the usual purposes.

The frictional resistance generating until the packing reaches the part 18 of the inner surface of the barrel, i.e. for an initial very short period, is the sum of that between the needle holding stopper and the barrel inner surface and that between the plunger end and the barrel inner surface, and then becomes, after the packing has passed the part 18 of the barrel inner surface, that between the plunger end and the barrel inner surface only and hence decreases significantly, since the resistance generated between the needle holding stopper and the barrel inner surface almost vanishes there.

After completion of the injection and when the plunger 2 is further pressed to release the lock having fixed the needle holding stopper 4, the spring reaches the state of its utmost compression. Consequently, when the force pressing the plunger is then reduced and the moment the spring starts pushing up the needle holding stopper and the plunger, the spring exerts the largest repulsive force. At this time, the frictional resistance against the spring is also the largest, and thereafter it decreases significantly as described above while the repulsive force of the spring gradually decreases, too. This means that the function of the spring is effectively utilized, whereby even a small spring is usable for this purpose.

Use of a small spring brings about many advantages; for example, the structural strength of the entire syringe can be decreased so that the barrel wall can be made thinner. As seen from FIG. 8, it is desirable to make the distance between the packing 24 and the point of the inner diameter difference 18 as short as possible, thereby minimizing the frictional resistance upon pushing up.

In the syringe of the present invention, before use, the needle holding stopper 4 is held by a lock mechanism from being pushed up toward the rear part of the barrel, and the needle end is generally protected with a plastic cap. When the syringe is used, after sterilization, the cap is removed from the needle and the plunger 2 is operated to suck an injection into the syringe. The injection is sucked into a space between the needle holding stopper and the plunger end and does not leak into a space between the needle holding stopper and the needle hole stopper, since sufficient airtightness is maintained at the contacting part of the needle holding stopper and the barrel inner surface.

After completion of injection, when the plunger is further pressed, the lock ring or stopper deforms to disengage the projections 29 and 29' from the recesses 28 and 28' through action of cams 30 and 30' and 31 and 31' and the lock becomes disengaged. Then, when the force pressing the plunger is decreased, the needle holding stopper is pushed up by force of the spring. On this occasion, the needle holding stopper is pushed up, passing the position where it had been locked without being locked again, until the spring resumes its original shape. Thus, the needle connected with the holding stopper is hangared in the barrel 1.

Since a silicone lubricant is generally used for syringes, the above mechanism parts move markedly smoothly.

The syringe of the present invention can, with its simple mechanism, safely hangar the needle in the barrel by a single finger motion, in order to prevent infection of virus and the like. The once hangared needle can never come out again, however, roughly it may be handled. Furthermore, the needle hole on the barrel end is closed so that the blood or the like of the patient adhered on the needle tip can never ooze out. The syringe further has such a structure that it is not reusable after use.

Use of this syringe can produce a marked effect in preventing infection of the virus and the like, and so is also effective in preventing infection of AIDS, which is a large problem in the world.

Obviously, numerous modifications and variations of the present invention are possible in light of the above teachings. It is therefore to be understood that within the scope of the appended claims, the invention may be practiced otherwise than as specifically described herein.

What is claimed is:

1. A syringe with needle-hangaring mechanism comprising a barrel, a plunger, a needle, a first needle holding stopper, a second needle hole stopper, a spring connecting said first needle holding stopper and said second needle hole stopper and a lock mechanism provide between said barrel and said first needle holding stopper, said barrel comprising a forward part having a smaller inside diameter and a rear part having a larger diameter, said two parts being connected with each other at a connecting point having an diameter difference, said lock mechanism functioning, in combination with said spring and said first needle hole stopper, such that it holds said first needle holding stopper, until completion of injection, so that said first needle holding stopper is pushed up into said rear part of said barrel, and that it is released when said plunger is further pressed after completion of the injection, so that, by force of said spring, said first needle holding stopper is pushed up, thereby hangaring said needle in said barrel, and said first needle hole stopper is moved to stopper the needle hole on the barrel end.

2. The syringe with needle-hangaring mechanism according to claim 1, wherein said needle hole stopper has a small hole through which said needle penetrates and is held, and said spring and said needle hole stopper, in combination, function such that, after said lock mechanism has been released and when said needle holding stopper is pushed up and said needle slips off said small hole, said needle hole stopper moves by force of said spring to stopper said needle hole.

3. The syringe with needle-hangaring mechanism according to either claim 1 or claim 2, wherein said lock mechanism comprises:

a pair of recesses provided on the inner surface of the syringe barrel, an elliptical lock ring fit in said recesses, and an end of said plunger comprising, from the forwardmost side, a conical part and cylindrical parts having outside diameters matching the inside diameters of said forward part and rear part of said barrel; and functions such that:

said lock ring holds, until completion of injection, the backward end of said first needle holding stopper so that said first needle holding stopper is not pushed up into said rear part of said barrel, and after completion of injection and when said plunger is further pressed down, said lock ring deforms by action of said parts of said packing from an elliptical to nearly a circular shape, thereby disengaging with said recesses so that said first needle holding stopper is pushed up by force of said spring, in the course of which pushing-up said lock ring is held on said part of said packing and remains nearly circular and hence cannot be locked again.

4. The syringe with needle-hangaring mechanism according to either claim 1 or claim 2, wherein said lock mechanism comprises:

a ring-shaped projection provided on the inner surface of said rear part of said barrel, a stopper comprising a hollow cylinder with its thin wall inclined inwardly upwardly and at least two small strips with their tips inclined outwardly and mounted on the large diameter-side circumference of said hollow cylinder;

an end of said plunger having, from the forwardmost side, a conical part and cylindrical parts having outside diameters matching the inside diameters of said forward part and rear part of said barrel; and functions such that:

said stopper holds, until completion of injection, the backward end of said first needle holding stopper so that said first needle holding stopper is not pushed up into said rear part of said barrel, and after completion of injection and when said plunger is further pressed down, said stopper becomes turned back by action of said conical parts of said end, thereby bending said strips inwardly so that locking is released and cannot be effected again when said first needle holding stopper is pushed up by force of said spring.

5. The syringe with needle-hangaring mechanism according to either claim 1 or claim 2, wherein said lock mechanism comprises:

recesses and cams provided on the inner surface of said barrel, and projections and cams provided on a part of said first needle holding stopper and contacting the inner surface of said barrel; and functions such that:

said projections are, until completion of injection, engaged with said recesses, thereby fixing said first needle holding stopper, and after completion of injection and when said plunger is further pressed down, said projections having fixed said first needle holding stopper are pushed down to be disengaged with said recesses and, at the same time, to cause said first needle holding stopper to rotate by action of said cams, so that no locking can be effected again when said first needle holding stopper is pushed up by force of said spring.

* * * * *

UNITED STATES PATENT AND TRADEMARK OFFICE
CERTIFICATE OF CORRECTION

PATENT NO. : 5,342,310
DATED : August 30, 1994
INVENTOR(S) : Ukio Ueyama; Shinichi Koni It is certified that error appears in the above-indentified patent and that said Letters Patent is hereby corrected as shown below:

COLUMN 1:

Claim 1, line 13, change "first" to --second--;

line 16, change "is pushed" to --is not pushed--;

line 21, change "first" to --second--.

Signed and Sealed this

Second Day of May, 1995

*Attest:*

BRUCE LEHMAN

*Attesting Officer*     *Commissioner of Patents and Trademarks*